US008778356B2

(12) United States Patent
Prior et al.

(10) Patent No.: US 8,778,356 B2
(45) Date of Patent: Jul. 15, 2014

(54) VACCINE

(75) Inventors: Joann Lisa Prior, Salisbury (GB); Sarah Victoria Harding, Salisbury (GB); Rachel Elizabeth Dean, Salisbury (GB); Timothy Phillip Atkins, Salisbury (GB)

(73) Assignee: The Secretary of State for Defence (GB)

( * ) Notice: Subject to any disclaimer, the term of this patent is extended or adjusted under 35 U.S.C. 154(b) by 0 days.

(21) Appl. No.: 13/144,119

(22) PCT Filed: Jan. 13, 2010

(86) PCT No.: PCT/GB2010/000044

§ 371 (c)(1), (2), (4) Date: Sep. 12, 2011

(87) PCT Pub. No.: WO2010/082020
PCT Pub. Date: Jul. 22, 2010

(65) Prior Publication Data

US 2012/0020993 A1 Jan. 26, 2012

(30) Foreign Application Priority Data

Jan. 13, 2009 (GB) .................................. 0900455.7

(51) Int. Cl.
*A61K 39/02* (2006.01)
*A61K 39/108* (2006.01)
*A61K 39/385* (2006.01)
*A61K 31/70* (2006.01)

(52) U.S. Cl.
USPC ................ 424/234.1; 424/197.11; 424/260.1; 514/23

(58) Field of Classification Search
USPC .......... 424/184.1, 190.1, 193.1, 234.1, 246.1, 424/197.11; 536/23.2, 23.4; 514/23
See application file for complete search history.

(56) References Cited

U.S. PATENT DOCUMENTS

| | | | |
|---|---|---|---|
| 4,235,871 | A | 11/1980 | Papahadjopoulos et al. |
| 4,235,877 | A | 11/1980 | Fullerton |
| 4,501,728 | A | 2/1985 | Geho et al. |
| 4,837,028 | A | 6/1989 | Allen |
| 4,879,213 | A | 11/1989 | Fox et al. |
| 5,019,369 | A | 5/1991 | Presant et al. |
| 5,187,074 | A | 2/1993 | Treiber et al. |
| 5,192,668 | A | 3/1993 | Treiber et al. |
| 5,278,302 | A | 1/1994 | Caruthers et al. |
| 5,308,854 | A | 5/1994 | Hoffman, Jr. et al. |
| 5,338,543 | A | 8/1994 | Fitzgerald et al. |
| 5,413,999 | A | 5/1995 | Vacca et al. |
| 5,476,874 | A | 12/1995 | Hungate et al. |
| 5,502,060 | A | 3/1996 | Thompson et al. |
| 5,565,205 | A | 10/1996 | Petersen et al. |
| 5,578,597 | A | 11/1996 | Spector et al. |
| 5,663,169 | A | 9/1997 | Young et al. |
| 5,703,055 | A | 12/1997 | Felgner et al. |
| 5,846,978 | A | 12/1998 | Coburn et al. |
| 6,429,199 | B1 | 8/2002 | Krieg et al. |
| 6,761,914 | B2 | 7/2004 | Deckers et al. |
| 7,955,601 | B2 | 6/2011 | Elvin et al. |
| 8,425,913 | B2 | 4/2013 | Elvin et al. |
| 2009/0220548 | A1 | 9/2009 | Elvin et al. |
| 2010/0055123 | A1 | 3/2010 | Harland |
| 2010/0062022 | A1 | 3/2010 | Harding et al. |
| 2011/0236423 | A1 | 9/2011 | Elvin et al. |

FOREIGN PATENT DOCUMENTS

| | | |
|---|---|---|
| EP | 0362278 | 4/1990 |
| EP | 0109942 | 3/1991 |
| EP | 0468520 | 1/1992 |
| EP | 0761819 A1 | 12/1997 |
| EP | 1874806 B1 | 2/2010 |
| GB | 2345061 | 6/2000 |
| WO | 8809797 | 12/1988 |
| WO | 9517210 | 6/1995 |
| WO | 9526204 | 10/1995 |
| WO | 9633739 | 10/1996 |
| WO | WO-9710351 | 3/1997 |
| WO | 9815287 | 4/1998 |
| WO | 0056282 | 9/2000 |
| WO | 0056361 | 9/2000 |
| WO | 0056362 | 9/2000 |
| WO | 0155398 | 8/2001 |
| WO | 03073351 | 9/2003 |
| WO | 2004006857 | 1/2004 |
| WO | 2006109071 | 10/2006 |
| WO | WO-2007036735 | 4/2007 |
| WO | 2010/082020 | 7/2010 |

OTHER PUBLICATIONS

Ngugi et al. Vaccine 28: 75551-7555, Sep. 15, 2010.*
Anuntagool et al. Microbiol. Immunol. 46: 143-150, 2002, abstract.*
UniProt Database Accession No. Q62CY2, Oct. 25, 2004.
UniProt Database Accession No. Q63M21, Oct. 25, 2004.
NCBI Database Accession No. YP_110850, Sep. 1, 2004.
NCBI Database Accession No. YP_110888, Sep. 1, 2004.
NCBI Database Accession No. YP_111684, Sep. 1, 2004.
NCBI Database Accession No. YP_111854, Sep. 1, 2004.
NCBI Database Accession No. CAH 36280, Sep. 1, 2004.
NCBI Database Accession No. CAH35556, Sep. 1, 2004.
NCBI Database Accession No. CAH39624, Sep. 1, 2004.
NCBI Database Accession No. AAU45954, Sep. 22, 2004.
NCBI Database Accession No. AAU47551, Sep. 22, 2004.
NCBI Database Accession No. AAU47807, Sep. 22, 2004.
"NCBI Database Accession No. BX571965, Sep. 1, 2004", bases 1804529-1805555 & 2743305- 2743985, Sep. 1, 2004.
"NCBI Database Accession No. BX571966", bases 2898490-2900025, Sep. 1, 2004.
U.S. Appl. No. 11/911,541, "Office Action" Feb. 21, 2012.
U.S. Appl. No. 11/911,541, "Office Action Response" Dec. 28, 2011.
U.S. Appl. No. 13/154,015, "Office Action" Jun. 5, 2012.
U.S. Appl. No. 13/154,015, "Office Action" Feb. 13, 2012.

(Continued)

*Primary Examiner* — S. Devi

(74) *Attorney, Agent, or Firm* — Kilpatrick Townsend & Stockton LLP; Dean W. Russell; Elena S. Polovnikova

(57) ABSTRACT

The present invention relates to a pharmaceutical formulation comprising lipopolysaccharide derived from *Burkholderia thailandensis* and its various uses, including but not limited to its use in the treatment and/or prophylaxis of meliodosis or amelioration of symptoms associated therewith, and/or glanders or amelioration of symptoms associated therewith.

15 Claims, 1 Drawing Sheet

(56) References Cited

OTHER PUBLICATIONS

U.S. Appl. No. 13/154,012, "Office Action Response" May 14, 2012.
U.S. Appl. No. 11/911,541, "Response to Election/Restriction Requirement" Sep. 19, 2012.
Anuntagool et al., "Antigenic Heterogeneity of Lipopolysaccharide Among *Burkholderia pseudomallei* Clinical Isolates", Southeast Asian J. Trop. Med. Public Health, 2000, vol. 31 (Suppl. 1): 146-152.
Atkins et al., "Characterisation of an acapsular mutant of *Burkholderia pseudomallei* identified by signature tagged mutagenesis", Journal Medical Microbiology, 2002, vol. 51(7); 539-547.
Atkins et al., "The identification and evaluation of ATP binding cassette systems in the intracelluar bacterium *Francisella tularensis*", Research in Microbiology, 2006, 157: 593-604.
Brett et al., "Pathogenesis of and immunity to melioidosis", Acta Tropica, 2000, 74:201-210.
Brett et al., "Structural and Immunological Characterization of *Burkholderia pseudomallei* O-Polysaccharide-Flagellin Protein Conjugates", Infection and Immunity, Jul. 1996, 64(7):2824-2828.
Bryan et al., "Passive protection of diabetic rats with antisera specific for the polysaccharaide portion of the lipopolysaccharide islodated from *Pseudomonas pseudomallei*", Can. J. Infect. Dis, Jul./Aug. 1994, 5(4): 170-178.
Cooper et al., "Safety and immunogenicity of CPG 7909 injection as an adjuvant to Fluarix influenza vaccine", Vaccine, 2004, vol. 22, 3136-3143.
Dalsgaard , "Saponin Adjuvants", Aarchiv fur die gesamte Virusforchung 44: 243-254, 1974.
Elvin et al., "Protection against Heterologous *Burkholderia pseudomallei* Strains by Dendritic Cell Immunization", Infection and Immunity, Mar. 2006, 74(3):1706-1711.
Garmory et al., "ATP-Binding Cassette Transporters are Targets for the Development of Antibacterial Vaccines and Therapies", Infection and Immunity, Dec. 2004, vol. 72(12) pp. 6757-6763.
Gilmore et al., "Use of Antigens Derived from *Burkholderia pseudomallei*, *B. thailandensis*, and *B. cepacia* in the Indirect Hemagglutination Assay for Melioidosis", Clinical and Vaccine Immunology, Nov. 2007, vol. 14(11) 1529-1531.
Golovliov et al., "Cytokine Expression in the Liver during the Early Phase of Murine Tularemia", Infection and Immunity, Feb. 1995, 63(2):534-538.
Harding et al., "The identification of surface proteins of Burkholderia pseudomallei", Vaccine, 2007, vol. 25, pp. 2664-2672.
Healey et al., "Humoral and Cell-Mediated Adaptive Immune Responses Are Required for Protection against *Burkholderia pseudomallei* Challenge and Bacterial Clearance Postinfection", Infection and Immunity, Sep. 2005, 73(9): 5945-5951.
Higgins et al., "ABC Transporters: From Microorganisms to Man", Annu. Rev. Cell Biol., 1992, 8:67-113.
Ho et al., "Specificity and Functional Activity of Anti-*Burkholderia pseudomallei* Polysaccharide Antibodies", Infection and Immunity, Sep. 1997, 65(9): 3648-3653.
Holden et al., "Genomic plasticity of the causative agent of melioidosis, *Burkholderia pseudomallei*", PNAS, Sep. 28, 2004, vol. 101, No. 39, pp. 14240-14245.
Isshiki et al., "Separation of 6-deoxy-heptane from a smooth-type lipopolysaccharide preparation of *Burkhoderia pseudomallei*", FEMS Microbiology Letters, 2001, 199:21-25.
Jakob et al., "Activation of Cutaneous Dendritic Cells by CpG-Containing Oligodeoxynucleotides: A Role for Dendritic Cells in the Augmentation of Th1 Responses by Immunostimulatory DNA1", J. Immunol., 1998, 161:3042-3049.
Jones et al., "Passive protection against *Burkholderia psudomallei* infection in mice by monoclonal antibodies against capsular polysaccharide, lipopolysaccharide or proteins", J. Med. Microbiol., 2002, 51:1055-1062.
Le et al., "Safety, tolerability and humoral immuse responses after intramuscular administration of a malaria DNA vaccine to healthy adult volunteers", Vaccine, 2000, 18:1893-1901.
Lipman et al., "Rapid and Sensitive Protein Similiarity Searches", Science, 1985, 227:1435-1441.
Matsuura et al., "Biological activities of lipopolysaccharide of *Burkholderia (Pseudomonas) pseudomallei*", FEMS Microbiol. Lett., 1996, 137:79-83.
Nierman et al., "Structural flexibility in the *Burkholderia mallei* genome", PNAS, Sep. 28, 2004, vol. 101, No. 39, 14246-14251.
Plotkin et al., "New Technologies for Making Vaccines", Vaccines, W. B. Saunders Co., 1988, p. 571.
Reckseidler et al., "Detection of Bacterial Virulence Genes by Subtractive Hybridization: Identification of Capsular Polysaccharide of *Burkholderia pseudomallei* as a Major Virulence Determinant", Infection and Immunity, 2001.
Reckseidler-Zenteno et al., "The Capsular Polysaccharide of *Burkhoderia pseudomallei* Contributes to Survival in Serum by Reducing Complment Factor C3b Deposition", Infection and Immunity, 2005, 73(2):1106-1115.
Reed et al., "A Simple Method of Estimating Fifty Per Cent Endpoints", Am. J. Hygiene, 1938, 27(3):493-497.
Sizemore et al., "Attenuated baceteria as a DNA delivery vehicle for DNA-mediated immunication", Vaccine, 1997, 15: (8)804-807.
Szoka, Jr. , "Comparative Properties and Methods of Preparation of Lipid Vesicles (Liposomes)", Ann. Rev. Biophys. Bioeng., 1980, 9:467-508.
Titball et al., "Vaccination against bubonic and pneumonic plage", Vaccine, 2001, 19(30):4175-4184.
Tiyawisutsri et al., "Antibodies from Patients with Melioidosis Recognize *Burkholderia mallei* but Not *Burkholderia thailandensis* Antigens in the Indirect Hemagglutination Assay", Journal of Clinical Microbiology, Sep. 2005, vol. 43(9), pp. 4872-4874.
Ulett et al., "A model of immunity to *Burkholderia pseudomallei*: unique responses following immunization and acute lethal infection", Microbes and Infection, 2005, 7:1263-1275.
Vedros et al., "Experimental vaccine against *Pseudomonas pseudomallei* infections in captive cetaceans", vol. 5, 157-161, 1988.
Velez et al., "Failure of a Killed Leishmania Amazonensis vaccine against American cutaneous leishmaniasis in Colombia", Trans. R. Soc. Trop. Med. Hyg., 2005, 99(8):593-598.
Woo et al., "Cloning and characterisation of malE in *Burkholderia pseudomallei*", J. Med. Microbiol., 2001, vol. 50 pp. 330-338.
Woo et al., "groEL Encodes a Highly Antigenic Protein in *Burkholderia pseudomallei*", Clinical and Diagnostic Laboratory Immunology, Jul. 2001, vol. 8, No. 4, pp. 832-836.
GB0900455.7 Search Report dated Apr. 22, 2009.
GB1000522.1 Search Report dated May 18, 2010.
WO2010082020 International Search Report mailed Jun. 9, 2010.
Anuntagool, et al., "Antigenic Relatedness between *Burkholderia pseudomallei* and *Burkholderia mallei*", Microbiol. Immunol. 46(3), 2002, pp. 143-150.
Anuntagool, et al., "Lipopolysaccharide from Nonvirulent Ara+ *Burkholderia pseudomallei* Isolates Is Immunologically Indistinguishable from Lipopolysaccharide from Virulent Ara- Clinical Isolates", Clinical and Diagnostic Laboratory Immunology, Mar. 1998, pp. 225-229.
Brett, et al, "The wbiA locus is required for the 2-O-acetylation of lipopolysaccharides expressed by *Burkholderia pseudomallei* and *Burkholderia thailandensis*", FEMS Microbiology Letters 218, 2003, pp. 323-328.
Iihara, et al., "Rapid Multiplex Immunofluorescent Assay to Detect Antibodies against *Burkholderia pseudomallei* and Taxonomically Closely Related Nonfermenters", Jpn. J. Infect. Dis., 2007, vol. 60, pp. 230-234.
Ilyukhin, et al., "*Burkholderia thailandensis*: Biological properties, identification, and taxonomy", Molekulyamaya Genetika Mikrobiologiya i Virusologiya, English abstract, 2002, 7-11.
Nelson, et al., "Evaluation of lipopolysaccharides and capsular polysaccharide as subunit vaccines against experimental melioidosis", J. Med. Microbial., 2004, vol. 53, pp. 1177-1182.
Qazi, et al., "Sero-characterization of lipopolysaccharide from *Burkholderia thailandensis*", Transactions of the Royal Society of Tropical Medicine and Hygiene, 2008, vol. 102/S1, pp. S58-S60.

(56) References Cited

OTHER PUBLICATIONS

Sarkar-Tyson, et al., "Protective efficacy of heat-inactivated *B. thailandensis, B. mallei* or *B. pseudomallei* against experimental melioidosis and glanders", Vaccine 27, 2009, pp. 4447-4451.

Warawa, et al., "Melioddosis vaccines", Expert Rev. Vaccines 1 (4), 2002, 477-482.

Wuthiekanun, et al., "Short Report: A Rapid Method for the Differentiation of *Burkholderia pseudomallei* and *Burkholderia thailandensis*", American Journal of Tropical Medicine and Hygiene, 2002, vol. 66, pp. 759-761.

Notice of Allowance dated Jan. 27, 2011 in related U.S. Appl. No. 12/088,748, 7 pages.

Office Action dated Dec. 7, 2011 in in related U.S. Appl. No. 13/154,015, 6 pages.

Advisory Action dated Sep. 12, 2012 in related U.S. Appl. No. 13/154,015, 11 pages.

Amendment and Response to Advisory Action dated Oct. 5, 2012 in related U.S. Appl. No. 13/154,015, 15 pages.

Advisory Action dated Oct. 19, 2012 in related U.S. Appl. No. 13/154,015, 3 pages.

Supplementary Amendment and Response to Advisory Action dated Nov. 29, 2012 in related U.S. Appl. No. 13/154,015, 10 pages.

Notice of Allowance dated Dec. 26, 2012 in related U.S. Appl. No. 13/154,015, 5 pages.

\* cited by examiner

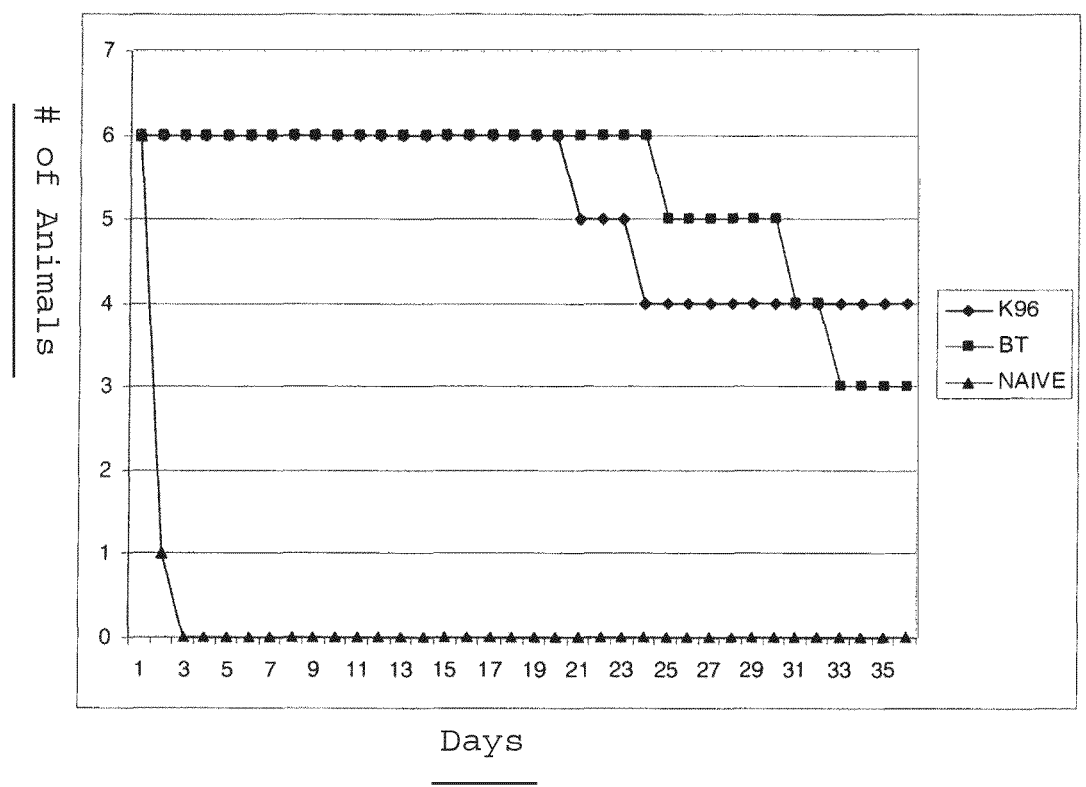

VACCINE

CROSS REFERENCE TO RELATED APPLICATIONS

This application is the U.S. national phase of International Application No. PCT/GB2010/000044 filed on Jan. 13, 2010 and published in English on Jul. 22, 2011 as International Publication No. WO 2010/082020 A1, which application claims priority to Great Britain Patent Application No. 0900455.7 filed on Jan. 13, 2009, the contents of both of which are incorporated herein by reference.

The present disclosure relates to pharmaceutical formulations comprising lipopolysaccharide (LPS) derived from *Burkholderia thailandensis*, for example for use in the treatment and/or prophylaxis of melioidosis or amelioration of symptoms associated therewith, and/or glanders or amelioration of symptoms associated therewith and use of LPS derived from *B. thailandensis*.

Melioidosis is an infectious disease caused by a gram-negative bacterium, *Burkholderia pseudomallei*, found in soil and water. It can be difficult to diagnose and is resistant to many common antibiotics. In up to 25% of patients, no focus of infection is found and the diagnosis is usually made on blood cultures or throat swab.

The bacteria are an intracellular pathogen, which can be latent in an infected individual for a number of years, such as 20 years or more. In fact the infection may not manifest itself until the infected patient's immune system is comprised.

Infection can lead to septicemia, and an 80-90% mortality rate is seen within 24-48 hours of the onset of these symptoms. Other symptoms of the disease include fever, pneumonia, abscesses including protastic abscesses, hepatosplenic abscesses, septic arthritis, osteomyelitis, neurological disease and pneumonia, closely mimicking tuberculosis (also an intracellular pathogen). The symptoms may last for months.

Melioidosis is endemic in parts of the world, for example south East Asia (including Thailand, Singapore, Malaysia, Burma and Vietnam) and northern Australia.

Diabetes mellitus seems to be a risk factor for developing the infection although otherwise healthy individuals can become infected. Other risk factors include thalassaemia, kidney disease, and occupation (rice paddy farmers are a high risk group for the infection). The source of infection is thought to be soil, mud and/or pooled surface water. The mode of infection is believed to be either through a break in the skin, or through the inhalation of aerosolized *B. pseudomallei*.

The treatment is divided into two stages, a high-dose intravenous antibiotic (such as ceftazidime) and an oral maintenance stage, for example with co-trimoxazole and doxycycline to prevent recurrence. Surgical drainage is usually indicated for prostatic abscesses and septic arthritis.

Given:
the debilitating nature of the infection,
that no prophylactic treatment/vaccine is available which is suitable for use in the general public, and
the infection is difficult to diagnose and treat,
an effective prophylactic therapy and/or treatment would be useful.

It is thought that passive immunotherapy with antibodies specific to the lipopolysaccharide (LPS), an endotoxin found in the exterior membrane of *B. pseudomallei*, can be employed to keep the symptoms of the infection from developing. LPS comprises Lipid A, core and O-antigen.

Some work has shown that inoculation with LPS from B. pseudomallei can provide some protection against subsequent challenge with the pathogen.

However, to date it is not possible to prepare the LPS synthetically and thus quantities of LPS for use in vaccination must be purified directly from the pathogen. *B. pseudomallei* handling requires containment level 3 facilities, which must be sealable to allow gaseous/vapourised disinfectant of the premise. Clearly the pathogen poses a risk to those handling it and preparing the LPS.

*B. thailandensis* is found in soil etc in Thailand and generally is a less virulent pathogen than *B. pseudomallei*. *B. thailandensis* synthesise O-antigen with the same repeating units as *B. pseudomallei*. Nevertheless, relatively little is known about the structural variety of LPS across the *Burkholderia* genus.

Some work, in a Thai population, (Tiyawisutri et al 2005 Antibodies from patients with melioidosis recognize *B. mallei* but not *B. thailandensis* antigens in the indirect hemagglutination assay J. Clin. Microbiol. 43:4872-4874) found there was no significant cross-reactivity with sera for patients diagnosed with melioidosis with *B. thailandensis* antigen preparations. In fact antibodies to *B. thailandensis* were not detected in sera from 84% of culture-confirmed cases of melioidosis. However, Gilmore et al (Use of Antigens Derived from *B. pseudomallei*, *B. thailandensis* and *B. cepacia* in the Indirect Hemagglutination Assay for Melioidosis Clinical and Vaccine Immunology, November 2007, p. 1529-1531) found that reactivity to *B. thailandensis* was seen in 88% of culture-positive sera, although the data set was not statistically significant. Qazi et al also showed some cross-reactivity of immune sera with 30-60 kDa LPS isolated from *B. thailandensis*. However, this cross-reactivity has not been identified with a particular portion or facet of the LPS, so it is not known if antibodies specific to LPS of *B. pseudomallei* can be generated in vivo by inoculation with LPS from *B. thailandensis*. Nor is it known if antibodies generated would be neutralising or protective against *B. pseudomallei* infection.

Furthermore, it is thought that *B. thailandensis* is ubiquitous in Thailand and that many individuals are naturally exposed to the bacteria. However, it is not known if this exposure to *B. thailandensis* can:

provide protection against infection with *B. pseudomallei*, although vaccination with genetically similar but non-pathogenic *B. thailandensis* only gave 50% protection after challenge with *B. pseudomallei* in a guinea-pig model of infection (Ilyukhin et al, 2002), which may suggest that *B. thailandensis* is not suitable for use as a vaccine against *B. pseudomallei*, and/or ensure that subsequent infection with *B. pseudomallei* is less severe that may otherwise have been the case.

Glanders is an infectious disease caused by the gram-negative bipolar bacterium *Burkholderia mallei*. In some respects the bacterium can considered to be a sub-species of *pseudomallei*.

Glanders most commonly occurs in horses, mules and donkeys, although it can infect other animals. Humans can be infected, for example by direct contact with infected animal or through inhalation of the pathogen or through skin abrasions.

Symptoms include ulceration of mucous membranes in the upper respiratory tract and the formation of lesions in the lungs, fever, nasal discharge and coughing. Acute forms of the illness can result in septicaemia.

Glanders is prevalent in Africa, Asia, Central and South America and the Middle East.

A treatment or prophylactic treatment for *B. mallei* infection such as glanders, would be useful.

The present inventors have now established that mice inoculated with an immunogenic component comprising at least O-antigen and core from *B. thailandensis* are able to withstand subsequent challenge with *B. pseudomallei*. This establishes that the LPS from *B. thailandensis* is similar enough in the relevant respects to LPS from *B. pseudomallei* to provide some protection from challenge with the pathogen *B. pseudomallei*.

This allows the preparation of a pharmaceutical formulation for the treatment/prophylaxis of infection with *B. pseudomallei* and/or *B. mallei*, employing components that are safe to handle and which are likely to be safer for administration than those prepared from *B. pseudomallei* or *B. mallei* because of being derived from a less virulent pathogen.

Thus in one aspect there is provided a pharmaceutical composition comprising an immunogenic component from *B. thailandensis* comprising at least O-antigen and core, and a pharmaceutically acceptable excipient.

The composition is thought to be useful in the treatment and/or prophylaxis of infection with *B. pseudomallei* and/or *B. mallei*.

BRIEF DESCRIPTION OF THE FIGURE

FIG. 1 shows the survival rate of mice challenged with *B. pseudomallei*

In one aspect the immunogenic component further comprises Lipid A or a detoxifed Lipd A.

Conjugation through the Lipid-A may result in detoxification. Alternatively acid hydrolysis may result is in partial detoxification.

The disclosure also extends to an immunogenic component comprising O-antigen and core from *B. thailandensis* and a heterologous carrier conjugated thereto.

In one aspect the immunogenic component is a conjugated to one, two or three carrier proteins, for example selected from tetanus toxoid (TT), diphtheria toxoid (DT), CRM 197 fragment C of tetanus toxoid or protein D. Examples of constructs include TT-LPS (or a LPS fragment), DT-LPS(or a LPS fragment), DT-TT-LPS(or a LPS fragment) or TT-DT-LPS(or a LPS fragment).

In one aspect the immunogenic components comprises a saccharide antigen, for example Hib.

In one embodiment the immunogenic component comprises one, two or three carrier proteins and a saccharide antigen, for example DT-TT-LPS(or a LPS fragment)-Hib.

The disclosure also extends to the conjugated or unconjugated component in a pharmaceutical preparation along with an excipient.

Component as employed herein refers to LPS, a fragment thereof, for example an immunogenic fragment thereof such as core and O-antigen, or a conjugate as described herein.

Immunogenic component as employed herein refers to a component which generates, stimulates and/or boosts an immune response.

Heterologous carrier as employed herein refers to a molecule derived from a source other than the Burkholderia family of pathogens.

In one or more embodiments the immunogen is in fact an antigen, that generates an antibody response, in particular a specific antibody response to a component of the disclosure, especially an antibody such as a neutralising antibody against the *B. pseudomallei* and/or *B. mallei*.

Suitable antibody responses may, for example include IgG responses.

Formulations

The component compositions according to the present disclosure maybe administered orally, topically, parenterally, transdermally, as a suppository or by any other pharmaceutically appropriate route.

Typical delivery routes include parenteral administration, e.g., intradermal, intramuscular or subcutaneous delivery. Other routes include oral administration, intranasal, intravaginal routes, intradermal and transdermal administration.

In one embodiment the antigen or composition according to the disclosure is provided optionally in either as a lyophilized formulation, for reconstitution later, or as a liquid formulation.

Transdermal administration may also be an effective method to deliver antigen or composition to muscle. Epidermal administration may also be employed. Thus the disclosure also extends to delivery by a transdermal patch, which may be occlusive or non-occlusive.

In one aspect the immunogenic component or composition comprising the same is coated onto an inert particle, for example a gold particle, for delivery into the dermis. The technique is sometimes referred as particle mediate epidermal delivery PMED. The particle may also comprise an adjuvant. Alternatively or additionally topically applied adjuvant, such as imiquimod, may be applied locally to the epidermis where the particle is to be delivered. The actives can also be formulated for administration via the nasal passages. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. For further discussions of nasal administration of certain vaccines, references are made to the following patents, U.S. Pat. Nos. 5,846,978, 5,663,169, 5,578,597, 5,502,060, 5,476,874, 5,413,999, 5,308,854, 5,192,668, and 5,187,074.

Compositions of use in the disclosure include liquid preparations, for an orifice, e.g., oral, nasal, anal, vaginal, etc. administration, such as suspensions, syrups or elixirs; and, preparations for parenteral, subcutaneous, intradermal, intramuscular or intravenous administration (e.g., injectable administration) such as sterile suspensions or emulsions. In compositions of the disclosure the relevant active ingredient(s) may be in admixture with a suitable carrier, diluent, or excipient such as sterile water, physiological saline, glucose or the like.

The active ingredients can be incorporated, if desired, into liposomes, microspheres or other polymer matrices (Feigner et al., U.S. Pat. No. 5,703,055; Gregoriadis, Liposome Technology, Vols. I to III (2nd ed. 1993), each of which is incorporated herein by reference). Liposomes, for example, which consist of phospholipids or other lipids, are nontoxic, physiologically acceptable and metabolizable carriers that are relatively simple to make and administer.

Liposome carriers may serve to target a particular tissue or infected cells, as well as increase the half-life of the active. Liposomes include emulsions, foams, micelles, insoluble monolayers, liquid crystals, phospholipid dispersions, lamellar layers and the like. In these preparations the vaccine to be delivered is incorporated as part of a liposome, alone or in conjunction with a molecule which binds to, e.g., a receptor prevalent among lymphoid cells, such as monoclonal antibodies or with other therapeutic or immunogenic compositions. Thus, liposomes either filled or decorated with a desired immunogen of the disclosure may be directed to the specific cells, where the liposomes then deliver the immunogen(s). Liposomes may be formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., Ann. Rev. Biophys. Bioeng. 9:467 (1980), U.S. Pat. Nos. 4,235,871, 4,501,728, 4,837,028, and 5,019,369.

The liposomes generally contain a neutral lipid, for example phosphatidylcholine, which is usually non-crystalline at room temperature, for example egg yolk phosphatidylcholine, dioleoyl phosphatidylcholine or dilauryl phosphatidylcholine.

Optionally the formulation may comprise an adjuvant, for example a known adjuvant formulation may be used to reconstitute a lyophilised formulation.

Immunogens/antigens employed in the disclosure may be mixed or adsorbed with adjuvants, which include but are not limited to alum, muramyl dipeptide and saponins such as Quil A. This may further boost the immune system's ability to deal with the infection.

Suitable adjuvants are those selected from the group of metal salts, oil in water emulsions, Toll like receptors agonist, (in particular Toll like receptor 2 agonist, Toll like receptor 3 agonist, Toll like receptor 4 agonist, Toll like receptor 7 agonist, Toll like receptor 8 agonist and Toll like receptor 9 agonist), saponins or combinations thereof. The level of free antigen in a given formulation may be increased by, for example, formulating the composition in the presence of phosphate ions, such as phosphate buffered saline, or by increasing the ratio of immunogen/antigen to metal salt. In one embodiment the adjuvant does not include a metal salt as sole adjuvant. In one embodiment the adjuvant does not include a metal salt.

In one embodiment the adjuvant does not consist of 3D-MPL (3-O-deacylated monophosphoryl lipid A). In one embodiment the adjuvant does not comprise 3D-MPL. 3D-MPL is an adjuvant which comprises detoxified lipid A from bacterial cell walls. Whilst not wishing to be bound by theory it is thought that combining MPL and the present immunogen in the quantities normally employed in vaccines overwhelms the immune system and therefore is not an optimised presentation.

An immunostimulant that may be suitable for use in the present disclosure is Quil A and its derivatives. Quil A is a saponin preparation isolated from the South American tree Quilaja Saponaria Molina and was first described as having adjuvant activity by Dalsgaard in 1974 ("Saponin adjuvants", Archiv. fur die gesamte Virusforschung, Vol. 44, Springer Verlag, Berlin, p243-254). Purified fragments of Quil A have been isolated by HPLC which retain adjuvant activity without the toxicity associated with Quil A (EP 0 362 278), for example QS7 and QS21 (also known as QA7 and QA21). QS21 is a natural saponin derived from the bark of Quillaja saponaria Molina which induces CD8+ cytotoxic T cells (CTLs), $Th_1$ cells and a predominant IgG2a antibody response.

Particular formulations of QS21 have been described which further comprise a sterol (WO 96/33739). The ratio of QS21:sterol will typically be in the order of 1:100 to 1:1 weight to weight.

Generally an excess of sterol is present, the ratio of QS21:sterol being at least 1:2 w/w. Typically for human administration QS21 and sterol will be present in a vaccine in the range of about 1 µg to about 100 µg, such as about 10 µg to about 50 µg per dose.

A formulation comprising QS21 and liposomes may be prepared, for example containing a charged lipid, which increases the stability of the lipsome-QS21 structure for liposomes composed of saturated lipids. In these cases the amount of charged lipid is often 1-20% w/w, such as 5-10%. The ratio of sterol to phospholipid is 1-50% (mol/mol), such as 20-25%.

The saponins may be separate in the form of micelles, mixed micelles (generally, but not exclusively with bile salts) or may be in the form of ISCOM matrices (EP 0 109 942), liposomes or related colloidal structures such as worm-like or ring-like multimeric complexes or lipidic/layered structures and lamellae when formulated with cholesterol and lipid, or in the form of an oil in water emulsion (for example as in WO 95/17210). The saponins may often be associated with a metallic salt, such as aluminium hydroxide or aluminium phosphate (WO 98/15287).

Usually, the saponin is presented in the form of a liposome, ISCOM or an oil in water emulsion.

Immunostimulatory oligonucleotides may also be used. Examples of oligonucleotides for use in adjuvants of the present disclosure include CpG containing oligonucleotides, generally containing two or more dinucleotide CpG motifs separated by at least three, more often at least six or more nucleotides. A CpG motif is a cytosine nucleotide followed by a guanine nucleotide. The CpG oligonucleotides are typically deoxynucleotides. In one embodiment the internucleotide in the oligonucleotide is phosphorodithioate, or more preferably a phosphorothioate bond, although phosphodiester and other internucleotide bonds are within the scope of the disclosure. Also included within the scope of the disclosure are oligonucleotides with mixed internucleotide linkages. Methods for producing phosphorothioate oligonucleotides or phosphorodithioate are described in U.S. Pat. No. 5,666,153, U.S. Pat. No. 5,278,302 and WO 95/26204.

Examples of oligonucleotides are as follows: TCC ATG ACG TTC CTG ACG TT (CpG 1826) SEQ ID NO:1 TCT CCC AGC GTG CGC CAT (CpG 1758) SEQ ID NO:2 ACC GAT GAC GTC GCC GGT GAC GGC ACC ACG SEQ ID NO:3 TCG TCG TTT TGT CGT TTT GTC GTT (CpG 2006) SEQ ID NO:4 TCC ATG ACG TTC CTG A TG CT (CpG 1668) SEQ ID NO:5 TCG ACG TTT TCG GCG CGC GCC G (CpG 5456) SEQ ID NO:6, the sequences may contain phosphorothioate modified internucleotide linkages.

Alternative CpG oligonucleotides may comprise one or more sequences above in that they have inconsequential deletions or additions thereto.

The CpG oligonucleotides may be synthesized by any method known in the art (for example see EP 468520). Conveniently, such oligonucleotides maybe synthesized utilising an automated synthesizer.

Examples of a TLR 2 agonist include peptidoglycan or lipoprotein. Imidazoquinolines, such as Imiquimod and Resiquimod are known TLR7 agonists. Single stranded RNA is also a known TLR agonist (TLR8 in humans and TLR7 in mice), whereas double stranded RNA and poly IC (polyinosinic-polycytidylic acid—a commercial synthetic mimetic of viral RNA) are exemplary of TLR3 agonists. 3D-MPL is an example of a TLR4 agonist whilst CpG is an example of a TLR9 agonist.

In one aspect the adjuvant comprises QS21. In one aspect the adjuvant comprises CpG. In one aspect the adjuvant comprises QS21 and CpG. In one aspect the adjuvant is formulated as an oil in water emulsion. In one aspect the adjuvant is formulated as liposomes.

The amount of CpG or immunostimulatory oligonucleotides in the adjuvants or vaccines of the present disclosure is generally small, but depending on the vaccine formulation maybe in the region of 1 to 1000 µg per dose, generally 1 to 500 µg per dose, and more such as between 1 to 100 µg per dose (10, 20, 30, 40, 50, 60, 70, 80 or 90 µg per dose).

The amount of saponin for use in the adjuvants of the present disclosure may be in the region of 1 to 1000 µg per dose, generally 1 to 500 µg per dose, more such as 1 to 250 µs per dose, and more specifically between 1 to 100 µg per dose (10, 20, 30, 40, 50, 60, 70, 80 or 90 µg per dose).

In one embodiment there is provided a formulations comprising a component according to the disclosure and QS21.

In one embodiment there is provided a formulation comprising a component according to the disclosure and CpG.

Thus in one embodiment there is provided a formulation comprising a component according to the disclosure and QS21 and CpG.

In one embodiment the formulation of the disclosure is for parenteral delivery, for example injection.

In one embodiment the formulation is a vaccine formulation.

Vaccine preparation is generally described in New Trends and Developments in Vaccines, edited by Voller et al., University Park Press, Baltimore, Md., U.S.A., 1978. Encapsulation within liposomes is described, for example, by Fullerton, U.S. Pat. No. 4,235,877.

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides may be employed, for example the use of lactose or glucose, particularly but not exclusively in the form of their hydrates. Particles for deposition in the lung require a particle size less than 10 microns, such as 1-9 microns for example from 0.1 to 5 µm, particularly from 1 to 5 µm. The particle size of the active (that is the antigen is of primary importance).

The propellant gases which can be used to prepare the inhalable aerosols are known from the prior art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellant gases may be used on their own or in mixtures thereof.

Particularly suitable propellant gases are halogenated alkane derivatives selected from among TG11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable propellants.

The propellant-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active.

In one embodiment of the disclosure the component or formulation herein is employed in a prime boost regime, as the priming and/or boosting dose. Priming in this context refers to priming the immune system. Boosting refer to increasing or sustaining the immune response of said priming.

In the one embodiment the dose of immunogenic component is in the range 1 pg to 1000 µg per Kg, such as 1 ng to 100 µg per Kg.

One aspect of the disclosure relates to an immunogenic conjugate comprising O-antigen and core derived from *B. thailandensis* and a heterologous carrier, for example as defined above.

In one aspect there is provided use of purified LPS from *B. thailandensis* or a fragment thereof (such as O-antigen and/or core), or a conjugate according to the disclosure in treatment, for example for treatment or prevention infection by *B. pseudomallei*, such as melioidosis, and/or *B. mallei* such as glanders, including reduction of the severity of subsequently developed symptoms and/or the amelioration of current symptoms.

The disclosure also extends to use of a composition comprising a component according to the disclosure for use in treatment, for example for treatment or prevention infection by *B. pseudomallei*, such as melioidosis and/or infection by *B. mallei* such as glanders, in particular melioidosis.

The disclosure also extends to use of a component herein or composition comprising the same for the manufacture of a medicament for the treatment or prophylaxis of infection by *B. pseudomallei*, such as melioidosis and/or infection by *B. mallei* such as glanders, in particular melioidosis.

In one embodiment the component/composition described herein reduces the severity of the symptoms of the melioidosis and/or glanders, in particular melioidosis.

In one embodiment there is provided a method of treatment comprising administering a therapeutically effective amount of component or composition according to the disclosure to a patient in need thereof.

In one embodiment the components/compositions of the present disclosure are administered in combination with other active pharmaceutical agents, such as one or more antibiotic compounds, for example ceftazidime or co-trimoxazole and/or doxycycline. The combination may be co-administration either concomitantly or sequentially, for example in the same 24 hour period. Co-trimoxazole and/or doxycycline may, for example be administered orally and may be maintenance therapy.

The LPS can be extracted from *B. thailandensis* employing the methods of Nelson et al 2004 J. Med Microbiol. 53, 1177-1182.

Derived from *B. thailandensis* in the context of the present specification is intended to refer to material extracted from the pathogen and optionally subjected to purification and/or processing, including conjugation, or alternatively characterised from the pathogen and then prepared recombinantly.

In the context of this specification "comprising" is to be interpreted as "including".

Aspects of the invention comprising certain elements are also intended to extend to alternative embodiments "consisting" or "consisting essentially" of the relevant elements.

EXAMPLES

Immunisation Regime

Groups of 6 female BALB/c mice (Charles River) of approximately 6 weeks of age were caged together with free access to food and water and subjected to a 12 h light/dark cycle. They were immunised intraperitoneally on days 1, 14 and 28 with 10 µg of *B. pseudomallei* LPS and *B. thailandensis* LPS. One group were not immunised with anything.

*B. pseudomallei* Challenge

All animals were intraperitoneally challenged on day 53 with $5.5\times10^4$ cfu of *B. pseudomallei* strain K96243. After challenge all animals were handled under containment level III conditions within an isolator compliant with British Standard BS5726. All investigations were perfomed in accordance with the Animal (Scientific Procedures) Act 1986. The animals were monitored for signs of disease for 5 weeks and culled at pre-determined humane end points. The results are shown in FIG. 1, where it can be seen that inoculation with LPS from *B. thailandensis* gave a similar level of protection to LPS derived from *B. pseudomallei.*

*B. mallei* Challenge

The above experiments can be repeated with *B. pseudomallei* replaced with *B. mallei.*

The invention claimed is:

1. A method of stimulating an immune response to *Burkholderia pseudomallei* in an individual comprising administering to the individual an amount of a composition comprising a lipopolysaccharide (LPS) isolated from *Burkholderia thailandensis*.

2. The method of claim 1, wherein the *Burkholderia pseudomallei* causes melioidosis.

3. The method of claim 1, wherein the LPS comprises lipid A or detoxified lipid A, O-antigen, and core.

4. The method of claim 3, wherein the LPS comprises the detoxified lipid A.

5. A method of stimulating an immune response to *Burkholderia pseudomallei* in a patient comprising administering to the patient an amount of a conjugate comprising a lipopolysaccharide (LPS) isolated from *Burkholderia thailandensis* and a heterologous carrier.

6. The method of claim 5, wherein the LPS comprises lipid A or detoxified lipid A, 0-antigen, and core.

7. The method of claim 5, wherein the heterologous carrier is tetanus toxoid, diphtheria toxoid, CRM197, or fragment C of tetanus toxoid.

8. The method of claim 6, wherein the LPS comprises the detoxified lipid A.

9. A method of immunizing an individual against *Burkholderia pseudomallei* comprising administering to the individual an amount of a lipopolysaccharide (LPS) isolated from *Burkholderia thailandensis*, or a conjugate comprising the isolated LPS and a heterologous carrier.

10. The method of claim 9, wherein the *Burkholderia pseudomallei* causes melioidosis.

11. The method of claim 9, wherein the lipopolysaccharide comprises lipid A or detoxified lipid A, O-antigen, and core.

12. The method of claim 11, wherein the LPS comprises the detoxified lipid A.

13. The method of claim 9, wherein the isolated lipopolysaccharide is administered to the individual.

14. The method of claim 9, wherein the conjugate comprising the isolated lipopolysaccharide and the heterologous carrier is administered to the individual.

15. The method of claim 14, wherein the heterologous carrier is tetanus toxoid, diphtheria toxoid, CRM197, or fragment C of tetanus toxoid.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial sequence
<220> FEATURE:
<223> OTHER INFORMATION: Synthetic sequence: Oligonucleotide

<400> SEQUENCE: 1
tccatgacgt tcctgacgtt                                                   20

<210> SEQ ID NO 2
<211> LENGTH: 18
<212> TYPE: DNA
<213> ORGANISM: Artificial sequence
<220> FEATURE:
<223> OTHER INFORMATION: Synthetic sequence: Oligonucleotide

<400> SEQUENCE: 2
tctcccagcg tgcgccat                                                     18

<210> SEQ ID NO 3
<211> LENGTH: 30
<212> TYPE: DNA
<213> ORGANISM: Artificial sequence
<220> FEATURE:
<223> OTHER INFORMATION: Synthetic sequence: Oligonucleotide

<400> SEQUENCE: 3
accgatgacg tcgccggtga cggcaccacg                                        30

<210> SEQ ID NO 4
<211> LENGTH: 24
<212> TYPE: DNA
<213> ORGANISM: Artificial sequence
<220> FEATURE:
<223> OTHER INFORMATION: Synthetic sequence: Oligonucleotide

<400> SEQUENCE: 4
tcgtcgtttt gtcgttttgt cgtt                                              24

<210> SEQ ID NO 5
<211> LENGTH: 20
<212> TYPE: DNA
<213> ORGANISM: Artificial sequence
<220> FEATURE:
<223> OTHER INFORMATION: Synthetic sequence: Oligonucleotide

<400> SEQUENCE: 5
tccatgacgt tcctgatgct                                                   20
```

```
<210> SEQ ID NO 6
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 6
tcgacgtttt cggcgcgcgc cg                                              22
```